(12) United States Patent
Rudolf

(10) Patent No.: US 9,983,149 B2
(45) Date of Patent: May 29, 2018

(54) BORE TESTING DEVICE

(71) Applicant: JENOPTIK Industrial Metrology Germany GmbH, Villingen-Schwenningen (DE)

(72) Inventor: Michael Rudolf, Constance (DE)

(73) Assignee: JENOPTIK Industrial Metrology Germany GmbH, Villingen-Schwenningen (DE)

( * ) Notice: Subject to any disclaimer, the term of this patent is extended or adjusted under 35 U.S.C. 154(b) by 170 days.

(21) Appl. No.: 14/871,354

(22) Filed: Sep. 30, 2015

(65) Prior Publication Data

US 2016/0187264 A1 Jun. 30, 2016

(30) Foreign Application Priority Data

Oct. 1, 2014 (DE) .................. 10 2014 114 304

(51) Int. Cl.
*G01N 21/00* (2006.01)
*G01N 21/954* (2006.01)
(Continued)

(52) U.S. Cl.
CPC ............ *G01N 21/954* (2013.01); *A61B 1/04* (2013.01); *A61B 1/06* (2013.01); *G01B 9/02* (2013.01);
(Continued)

(58) Field of Classification Search
CPC .... A61B 1/00; A61B 1/04; A61B 1/41; A61B 1/96; H01J 5/16; H05K 13/08
See application file for complete search history.

(56) References Cited

U.S. PATENT DOCUMENTS 5,739,525 A * 4/1998 Greve ............... H05K 13/08
250/216
8,334,971 B2 * 12/2012 Keller ............... G01N 21/954
356/237.2
(Continued)

FOREIGN PATENT DOCUMENTS

DE 3232904 C2 3/1994
DE 4320845 C1 10/1994
(Continued)

OTHER PUBLICATIONS

Ute Katranski, "Das dreidimensionale Computersehen—Shape from Shading" (124 pages) Publication Abstract, Published Nov. 13, 2013 (2 pages).

*Primary Examiner* — Sathyanaraya V Perungavoor
*Assistant Examiner* — Patricia I Young
(74) *Attorney, Agent, or Firm* — Shlesinger, Arkwright & Garvey LLP

(57) ABSTRACT

A testing device for testing an inner surface of a rotationally symmetrical cavity in a workpiece has a measuring head which defines an axial direction, and on which an optical system is situated. The optical system is in image transmission connection with an image recorder and a downstream evaluation apparatus. The testing device also has an illumination arrangement for illuminating an imaging area of the inner surface which is detected by the optical system. The illumination arrangement is designed and configured for illuminating the inner surface which is detected by the optical system. The illumination arrangement can illuminate the inner surface to be tested from different illumination directions in order to generate shadow images of the topography of the inner surface. The evaluation apparatus is designed and configured for determining the topography based on the shadow images recorded by the image recorder.

19 Claims, 2 Drawing Sheets

(51) Int. Cl.
| | |
|---|---|
| *A61B 1/00* | (2006.01) |
| *A61B 1/04* | (2006.01) |
| *H01J 5/16* | (2006.01) |
| *G01B 9/02* | (2006.01) |
| *C02F 1/32* | (2006.01) |
| *G01B 11/12* | (2006.01) |
| *A61B 1/06* | (2006.01) |
| *H04N 5/225* | (2006.01) |
| *H04N 5/232* | (2006.01) |
| *H04N 9/07* | (2006.01) |
| *G01B 11/22* | (2006.01) |
| *G01B 11/24* | (2006.01) |

(52) U.S. Cl.
CPC ....... *G01B 9/0209* (2013.01); *G01B 9/02021* (2013.01); *G01B 11/12* (2013.01); *G01B 11/22* (2013.01); *G01B 11/2441* (2013.01); *H04N 5/2256* (2013.01); *H04N 5/23238* (2013.01); *H04N 9/07* (2013.01); *G01N 2021/9544* (2013.01); *H04N 2005/2255* (2013.01)

(56) References Cited

U.S. PATENT DOCUMENTS

| | | |
|---|---|---|
| 9,261,359 B2 | 2/2016 | DeCool |
| 9,395,310 B2* | 7/2016 | Rudolf ................. G01N 21/954 |
| 9,562,756 B2 | 2/2017 | Seewig |
| 9,683,914 B2 | 6/2017 | Dietz et al. |
| 9,816,811 B2 | 11/2017 | Riester |
| 2006/0106283 A1* | 5/2006 | Wallace ............. A61B 1/00096 |
| | | 600/109 |
| 2009/0306474 A1* | 12/2009 | Wilson ................. A61B 1/041 |
| | | 600/109 |
| 2016/0187265 A1* | 6/2016 | Rudolf .................... G01B 9/02 |
| | | 356/496 |

FOREIGN PATENT DOCUMENTS

| | | |
|---|---|---|
| DE | 4416493 A1 | 11/1995 |
| DE | 10 2009 019 459 B4 | 12/2010 |
| WO | WO 2009/003692 | 1/2009 |

* cited by examiner

BORE TESTING DEVICE

CROSS-REFERENCE TO RELATED APPLICATIONS

This application claims the priority of German Application No. 10 2014 114 304.3, filed Oct. 1, 2014, which is incorporated herein by reference.

FIELD OF THE INVENTION

The present invention relates to a bore testing device for testing the inner surface of a bore in a workpiece.

BACKGROUND OF THE INVENTION

Bore testing devices of this type, also referred to as internal test sensors, are used to test the inner surfaces of bores, for example in the inspection of cylinder bores in crankcases. They are used for imaging the radial inner surface of the bore, and to check whether it meets predetermined requirements regarding surface quality.

Such devices are known from WO 2009/003692, DE 4416493 A1, DE 4320845 C1, and DE 3232904 C2, for example.

A bore testing device of this type for testing the inner surface of a bore in a workpiece is known from DE 10 2009 019 459 B4, having a measuring head which defines an axial direction, and on which an optical system is situated which is in image transmission connection with an image recorder and a downstream evaluation apparatus. The testing device known from this publication also has an illumination arrangement for illuminating an imaging area of the inner surface which is detected by the optical system. The testing device known from this publication allows quick, accurate testing of inner surfaces of cavities, for example bores.

OBJECTS AND SUMMARY OF THE INVENTION

An object of the invention is to provide a bore testing device of this type which is improved with regard to the detection of surface defects in a bore in a workpiece.

This object is achieved by the invention set forth herein.

This object is further achieved by a bore testing device for testing the inner surface of a bore in a workpiece, the bore testing device including a measuring head which defines an axial direction, and on which an optical system is situated which is in image transmission connection with an image recorder and a downstream evaluation apparatus. There is an illumination arrangement for illuminating an imaging area of the inner surface which is detected by the optical system. The illumination arrangement is configured for illuminating the inner surface to be tested from different illumination directions in order to generate shadow images of the topography of the inner surface, and an evaluation apparatus is provided and configured for determining the topography based on the shadow images recorded by the image recorder.

The basic concept of the invention is to modify known devices in such a way that it is suitable for determining the topography of the surface to be examined. On this basis, the invention is based on the concept of determining the topography of the surface based on shadow images.

The invention provides that the illumination arrangement is designed and configured for illuminating the inner surface to be tested from different illumination directions in order to generate shadow images of the topography of the surface. In addition, the invention provides that the evaluation apparatus is designed and configured for determining the topography based on the shadow images recorded by the image recorder.

According to the invention, the surface to be examined is thus illuminated from different illumination directions. The resulting shadow images are imaged by means of the optical system (imaging optics) and the image recorder (image sensor) and evaluated by the evaluation apparatus in order to determine the topography of the surface. The evaluation of the shadow images may take place, for example, using the "shape from shading" method, known per se.

As a result of the bore testing device according to the invention being designed and configured for determining the topography of the surface to be examined, it is possible not only to detect the presence of surface defects, but also to determine whether the surface defect is a depression. In other words, the testing device according to the invention allows depth information to be obtained concerning the surface to be examined, based on the recorded shadow images.

Faulty detections caused by surface soiling may be reduced in this way. In addition, it is possible to detect types of defects which are not detectable using the known testing devices.

A further advantage of the bore testing device according to the invention is that it has a relatively simple and compact design.

The number of different illumination directions from which the inner surface to be tested is illuminated may be selected within a wide range, depending on the particular requirements. According to the invention, it is sufficient in principle for the inner surface to be illuminated from two different illumination directions. To this end, one advantageous further embodiment of the invention provides that the illumination apparatus has at least one first light source arrangement for illuminating the inner surface from a first illumination direction, and a second light source arrangement for illuminating the inner surface from a second illumination direction. The illumination directions are selected in such a way that, within the scope of the desired accuracy of the assessment, meaningful shadow images are generated which are recorded by the image recorder. However, depending on the particular requirements, illumination from more than two illumination directions, in particular from four illumination apparatuses, may be provided. It is advantageous in particular when, for the four illumination directions, in each case two are situated opposite one another in pairs. If the axial direction defined by the measuring head is the z-axis, one illumination direction may extend in the positive z direction, and the other illumination direction may extend in the negative z direction. In such an arrangement, a third illumination direction may extend in the positive phi direction (peripheral direction of the inner surface to be examined), and the fourth illumination direction may extend in the negative phi direction. Such an arrangement allows detection and assessment of surface defects with great accuracy.

A further embodiment of the above-mentioned embodiment provides that the first light source arrangement is designed and configured for radially illuminating the surface, and the second light source arrangement is designed and configured for tangentially illuminating the inner surface in the peripheral direction.

In order to uniformly illuminate the inner surface of a bore in a workpiece, another advantageous further embodiment of the invention provides that at least one light source arrangement is designed and configured for rotationally symmetrical or approximately rotationally symmetrical illumination of the inner surface. In the context of the invention, a bore is understood to mean any rotationally symmetrical or approximately rotationally symmetrical recess in a workpiece, regardless of how the recess has been introduced into the workpiece, for example by drilling or by means of some other machining process, or by molding or the like. In the context of the invention, an approximately rotationally symmetrical recess is understood to mean that the basic shape of the recess is rotationally symmetrical, but may contain grooves or the like, for example. Within the meaning of the invention, a rotationally symmetrical recess is of course also understood to mean a recess whose basic shape deviates from rotational symmetry due to anomalies. According to the invention, an approximately rotationally symmetrical illumination of the inner surface is understood to mean that the maximum brightness of the illumination in the peripheral direction of the inner surface varies to an extent that the assessment of the generated shadow images is not adversely affected.

Another advantageous further embodiment of the invention provides that at least one light source arrangement has a plurality of light sources, preferably light-emitting diodes at least in part, arranged in a ring shape in the peripheral direction. Light-emitting diodes are available as simple, inexpensive standard components, and allow uniform illumination of the inner surface to be examined.

One extremely advantageous further embodiment of the invention provides that the illumination arrangement has at least two light source arrangements which are separated at a distance from one another in the axial direction, and which preferably irradiate in opposite directions. Such an arrangement allows an illumination of the inner surface to be examined from two illumination directions.

According to the invention, two opposite illumination directions may be achieved by separate light source arrangements. This applies in particular to light source arrangements which irradiate in the z direction. However, it is also possible according to the invention to achieve an illumination from two opposite illumination directions by means of the same light source arrangement by changing the irradiation direction of the light source arrangement.

Another advantageous further embodiment of the invention provides a control apparatus for controlling the light source arrangements.

A further embodiment of the above-mentioned embodiment provides that the control apparatus is designed and configured for chronologically successive illumination of the inner surface from the different illumination directions. For example and in particular, in this embodiment the particular measuring point may be illuminated on the inner surface from the different illumination directions in succession, and in each case a corresponding shadow image may be recorded by the image recorder. The number of shadow images, recorded corresponding to the number of illumination directions, may then be evaluated in the evaluation apparatus.

To speed up the testing operation, another advantageous further embodiment of the invention provides that a separate illumination color is associated with each illumination direction, and that the image recorder has a color sensor. In this embodiment, the particular measuring point is thus simultaneously illuminated, on the inner surface to be tested, from the different illumination directions, and in particular with a separate illumination color for each illumination direction, the resulting shadow images accordingly being combined into a single color image which is recorded by the image recorder. The shadow images thus contained in the resulting color image may be distinguished in the evaluation apparatus based on the different illumination colors, and evaluated separately in the required manner.

To test an inner surface along its axial direction, one advantageous further embodiment of the invention provides that an advancing apparatus for advancing the measuring head in the axial direction in a stepwise or continuous manner is associated with the measuring head.

According to the invention, it is possible in principle to use an optical system which views the particular measuring point the peripheral direction with a limited viewing angle, the optical system then being rotated about a rotational axis aligned with the axis of rotational symmetry of the cavity in order to completely test the inner surface in the peripheral direction. In this regard, one extremely advantageous further embodiment of the invention provides that the optical system is an optical system with a panoramic view. In this embodiment, the inner surface is recorded over a complete viewing angle of preferably 360 degrees, so that rotating the optical system is unnecessary in principle.

Another advantageous further embodiment of the invention provides that at least the measuring head, preferably the measuring head together with the illumination arrangement, is designed as an endoscope which is insertable into the cavity to be examined. Since the measuring head and the illumination arrangement of the testing device according to the invention in principle occupy only a relatively small installation space, according to the basic principle of the invention endoscopes may also be implemented which are insertable into relatively narrow bores.

The invention is explained in greater detail below with reference to the appended drawings, in which one embodiment of a bore testing device according to the invention is illustrated in a highly schematic manner. All features, alone or in any desired combination, described in the description, and illustrated in the drawings, constitute the subject matter of the present invention, regardless of their cross-reference to variations and combinations of the elements of the inventive bore testing device, and regardless of their wording or illustration in the description or drawings, respectively.

The evaluation of the shadow images which are generated by illumination from different illumination directions may, for example and in particular, take place according to the shape from shading method, known per se. The manner in which shadow images are evaluated within the scope of this known method is generally known to those of ordinary skill in the art, and therefore is not explained in greater detail here. With regard to the evaluation of the shadow images, reference is made, for example and in particular, to the publication *Das dreidimensionale Computersehen—Shape from Shading* (*Three-dimensional Computer Vision—Shape from Shading*), Author: Ute Katranski, VDM Verlag, 2008, ISBN:978-3-83648096-3.

Relative terms such as left, right, up, and down are for convenience only and are not intended to be limiting.

DETAILED DESCRIPTION OF THE INVENTION

Figure 1:
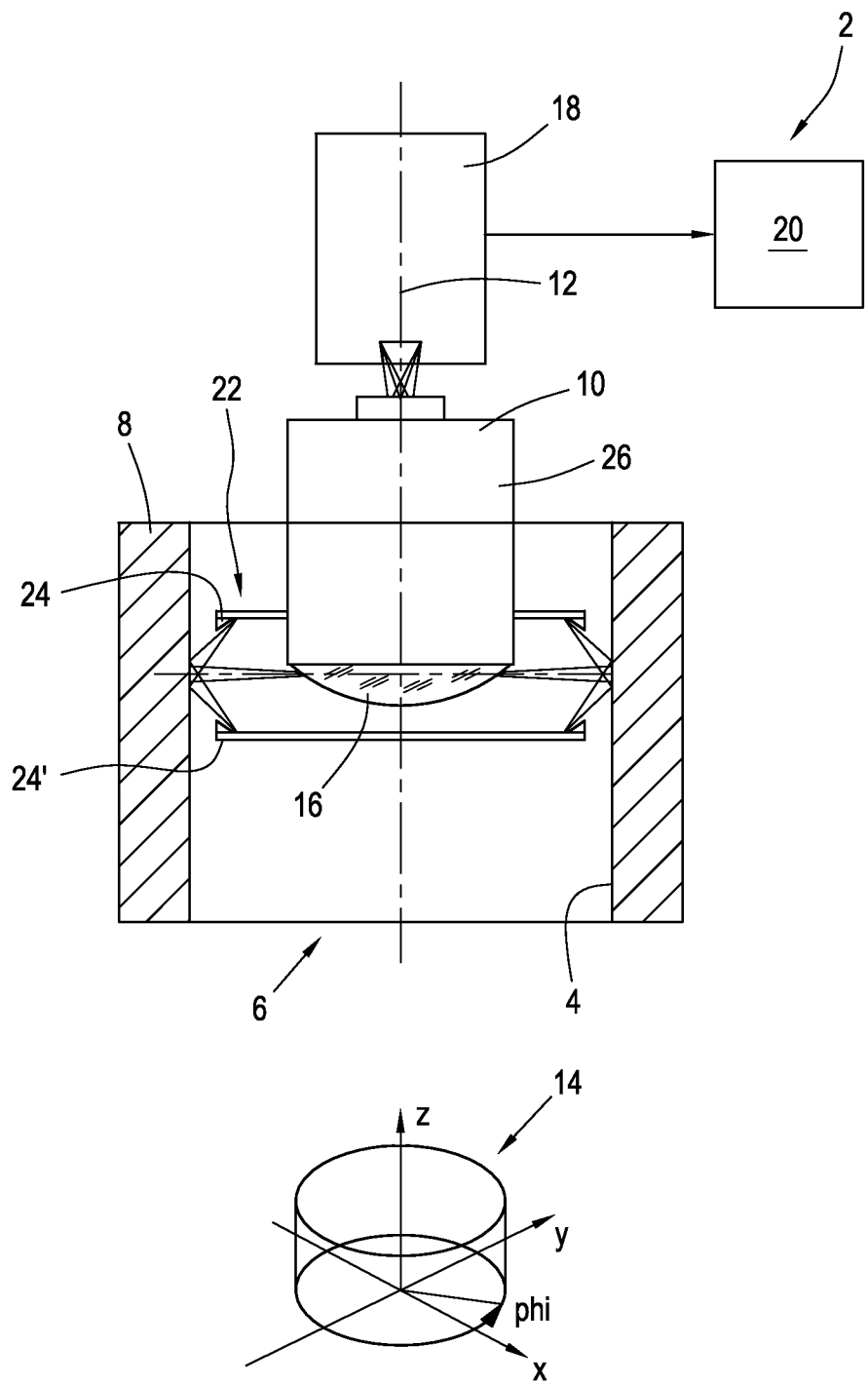
FIG. 1 is a view of one embodiment of a measuring head of a bore testing device according to the invention.
Figure 2:
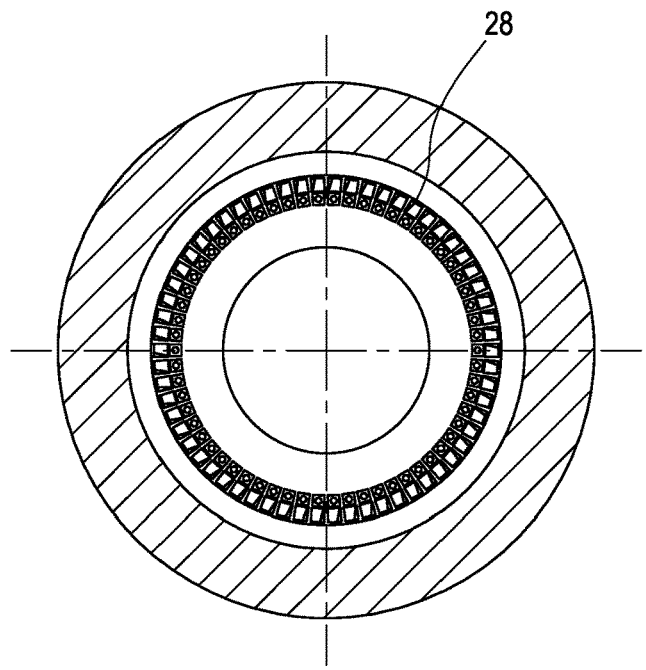
FIG. 2 is an axial view of the testing device according to FIG. 1.
Figure 3:
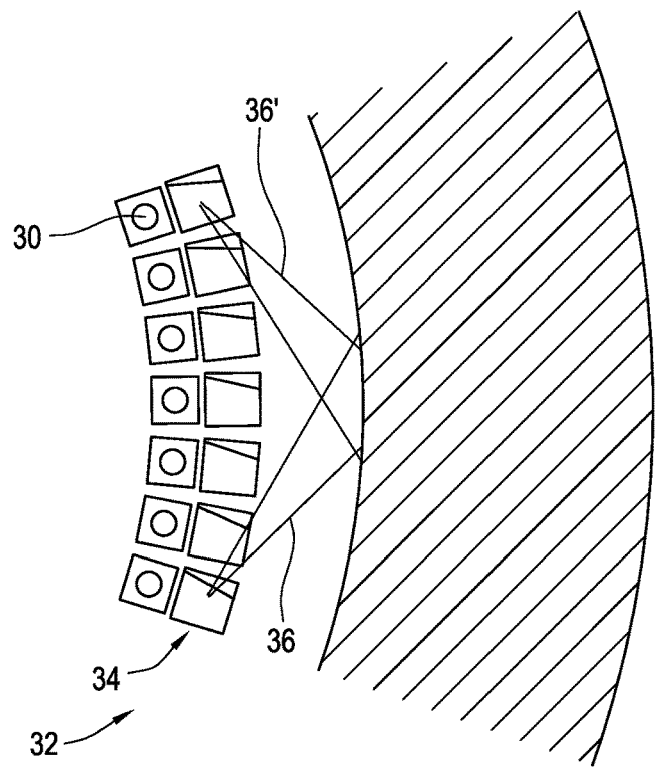
FIG. 3 is a detail from FIG. 2 in enlarged scale.

Reference is made to FIGS. 1 to 3 below for explaining the embodiment.

FIG. 1 illustrates in a highly schematic manner one embodiment of a bore testing device 2 according to the invention for testing an inner surface 4 of a rotationally symmetrical bore 6 in a workpiece 8 (bore inspection device), having a measuring head 10 which defines an axial direction by means of an axis, which is symbolized in FIG. 1 by a dash-dotted line 12.

A coordinate system 14 is depicted in FIG. 1, from which it is apparent that the z-axis corresponds to axis 12, and the peripheral direction is defined by the angle phi.

An optical system 16 (imaging optics) is situated on the measuring head 10, and in this embodiment is formed by an optical system having a panoramic view of 360 degrees. Accordingly, depending on the position of the measuring head 10 along the axis 12, the optical system 16 records a band on the inner surface 4 which extends over 360 degrees in the peripheral direction. The optical system 16 is in image transmission connection with a digital image recorder (camera) 18 and a downstream digital evaluation apparatus 20.

The bore testing device 2 also has an illumination arrangement 22 for illuminating an imaging area on the inner surface 4 which is detected (in a band shape) by the optical system.

According to the invention, the illumination arrangement is designed and configured for illuminating the inner surface 4 to be tested from different illumination directions in order to generate shadow images of the topography of the surface, the evaluation apparatus 20 being designed and configured for determining the topography based on the shadow images recorded by the image recorder.

In the illustrated embodiment, the illumination arrangement has a first light source arrangement 24 for illuminating the inner surface 4 from a first illumination direction, which in this embodiment corresponds to the negative z direction.

In addition, in the illustrated embodiment the illumination apparatus 22 has a third light source arrangement 24' (for the second light source arrangement 32, see reference numeral 32 in FIG. 3) which is used for illuminating the inner surface 4 from a second illumination direction, which in this embodiment corresponds to the positive z direction. As is apparent from FIG. 1, the light source arrangements 24, 24' are designed for radially illuminating the inner surface 4. Only the light source arrangement 24 is explained in greater detail below. The light source arrangement 24' has a corresponding design, and therefore is not explained in greater detail here.

The light source arrangement 24 has a ring-shaped support 28 (see FIG. 2) which is connected to the holder 26 of the optical system 16; light sources are situated on the support in a ring shape in the peripheral direction, and in this embodiment are formed by light-emitting diodes, of which only one light-emitting diode, provided with reference numeral 30 (see FIG. 3), is provided in the drawing. Due to the ring-shaped arrangement of the light-emitting diodes, the first light source arrangement 24 is thus designed for a rotationally symmetrical illumination of the inner surface 4 in the peripheral direction.

In the illustrated embodiment, the illumination apparatus 22 also has a second light source arrangement 32 which has a plurality of light sources arranged in a ring shape in the peripheral direction over an angle of 360 degrees, which in this embodiment are formed by light-emitting diodes 34 (see FIG. 3). The second light source arrangement 32 is designed and configured in such a way that in the tangential peripheral direction the light-emitting diodes 34, with the aid of suitable beam guiding elements, illuminate the inner surface 4 in the positive phi direction, as indicated by reference numeral 36 in FIG. 3, and/or in the negative phi direction, as indicated by reference numeral 36' in FIG. 3.

In the illustrated embodiment, the second light source arrangement 32 thus achieves an illumination of the inner surface 4 from opposite illumination directions, namely, a third illumination direction (positive phi direction) and a fourth illumination direction (negative phi direction).

During illumination of a measuring point on the inner surface 4, a different shadow image thus results in each of the four illumination directions. In the illustrated embodiment, the image recorder 18 can record a separate shadow image for each of the illumination directions. Accordingly, the light source arrangements 24, 24', 32 may thus be controlled in chronological succession by a control apparatus, not illustrated in greater detail, in such a way that the measuring point is illuminated in chronological succession from the four illumination directions, and in each case a resulting shadow image is recorded by the image recorder 18. The separately recorded shadow images may then be evaluated in the evaluation apparatus 20, for example according to the shape from shading method, so that the topography of the inner surface 4 at the measuring point may be determined in this way.

However, it is also possible according to the invention for a separate illumination color to be associated with each of the four illumination directions. This means that on the one hand the light source arrangements 24, 24' have different illumination colors. On the other hand, the light source arrangement 32 then has a design such that the light-emitting diodes which irradiate in the positive phi direction have a third illumination color, and the light-emitting diodes which irradiate in the negative phi direction have a fourth illumination color. A single color image which is composed of a superimposition of the shadow images generated by means of the individual illumination colors thus results from the illumination with the different illumination colors from the different illumination directions. This resulting color image is then recorded by a color sensor of the image recorder 18. The shadow images which are associated with the individual illumination directions, and thus associated with illumination colors, may then be distinguished, based on the colors, in the evaluation apparatus 20. The topography of the inner surface 4 may then in turn be determined from the individual shadow images.

If a surface anomaly at the inner surface 4 is identified by means of the bore testing device 2, it may be concluded, based on the determined topography, whether the surface anomaly is an elevation or a depression.

The bore testing device 2 according to the invention allows the testing of inner surfaces with great accuracy and speed, and faulty detections due to surface soiling are reduced. In addition, in the evaluation apparatus 20 it is possible to recognize types of defects which have not detectable heretofore.

As is apparent from FIG. 1, in the illustrated embodiment the measuring head 10 together with the illumination apparatus 22 is designed as an endoscope which is insertable into the bore 6.

To inspect the bore 6 along its axial extension, in the illustrated embodiment an advancing apparatus for advancing the measuring head in a stepwise or continuous manner in the axial direction, i.e., along the axis 12, is associated with the testing device 2.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. A bore testing device for testing an inner surface of a bore in a workpiece to detect surface defects in the bore in the workpiece, the bore testing device comprising:
   a) a measuring head which defines an axial direction, and on which an optical system is situated which is in image transmission connection with an image recorder and a downstream evaluation apparatus;
   b) an illumination arrangement is provided, the illumination apparatus illuminates an imaging area of the inner surface of the bore in the workpiece which is detected by the optical system;
   c) the illumination arrangement illuminates the inner surface of the bore in the workpiece to be tested from different illumination directions and generates shadow images of a topography of the inner surface of the bore in the workpiece;
   d) the downstream evaluation apparatus determines the topography based on the shadow images recorded by the image recorder;
   e) the illumination apparatus has a first light source arrangement which illuminates the inner surface from a first illumination direction, and a second light source arrangement which illuminates the inner surface from a second illumination direction;
   f) the first light source arrangement radially illuminates the inner surface, and the second light source arrangement tangentially illuminates the inner surface in the peripheral direction; and
   g) an advancing apparatus for advancing the measuring head in the axial direction in a stepwise manner is associated with the measuring head.

2. The testing device according to claim 1, wherein:
   a) one of the first and second light source arrangements is configured for rotationally symmetrical illumination of the inner surface.

3. The testing device according to claim 1, wherein:
   a) one of the first and second light source arrangements has a plurality of light sources arranged in a ring shape in the peripheral direction.

4. The testing device according to claim 3, wherein:
   a) the first and second light source arrangements include light-emitting diodes.

5. The testing device according to claim 1, wherein:
   a) the first and second light source arrangements are separated at a distance from one another in the axial direction, and irradiate in opposite directions.

6. The testing device according to claim 1, wherein:
   a) a control device is provided for controlling the first and second light source arrangements.

7. The testing device according to claim 6, wherein:
   a) the control device chronologically successively illuminates the inner surface from the different illumination directions.

8. The testing device e according to claim 1, wherein:
   a) a separate illumination color is associated with each of the first and second illumination directions; and
   b) the image recorder includes a color sensor.

9. The testing device according to claim 1, wherein:
   a) the optical system is an optical system with a panoramic view.

10. The testing device according to claim 1, wherein:
    a) the measuring head or the measuring head together with the illumination arrangement, is an endoscope which is insertable into the bore to be tested.

11. The testing device according to claim 1, wherein:
    a) the image recorder is a digital image recorder.

12. The testing device according to claim 1, wherein:
    a) the evaluation apparatus is a digital evaluation apparatus.

13. The testing device according to claim 1, wherein:
    a) the evaluation apparatus evaluates the shadow images recorded by the image recorder according to shape from the shading method.

14. A bore testing device for testing an inner surface of a bore in a workpiece to detect surface defects in the bore in the workpiece, the bore testing device comprising:
    a) a measuring head which defines an axial direction, and on which an optical system is situated which is in image transmission connection with an image recorder and a downstream evaluation apparatus;
    b) an illumination arrangement is provided, the illumination apparatus illuminates an imaging area of the inner surface of the bore in the workpiece which is detected by the optical system;
    c) the illumination arrangement illuminates the inner surface of the bore in the workpiece to be tested from different illumination directions and generates shadow images of a topography of the inner surface of the bore in the workpiece;
    d) the downstream evaluation apparatus determines the topography of the inner surface of the bore in the workpiece based on the shadow images of the topography of the inner surface of the bore in the workpiece recorded by the image recorder; and
    e) an advancing apparatus is provided, the advancing apparatus advances the measuring head in the axial direction in a stepwise manner.

15. The testing device according to claim 14, wherein:
    a) the illumination apparatus has a first light source arrangement for illuminating the inner surface from a first illumination direction, and a second lightsource arrangement for illuminating the inner surface from a second illumination direction.

16. The testing device according to claim 15, wherein:
    a) the first light source arrangement is configured for radially illuminating the inner surface, and the second light source arrangement is configured for tangentially illuminating the inner surface in the peripheral direction.

17. A bore testing device for testing an inner surface of a bore in a workpiece to detect surface defects in the bore in the workpiece, the bore testing device comprising:

a) a measuring head which defines an axial direction, and on which an optical system is situated which is in image transmission connection with an image recorder and a downstream evaluation apparatus;
b) an illumination arrangement is provided, the illumination apparatus illuminates an imaging area of the inner surface of the bore in the workpiece which is detected by the optical system;
c) the illumination arrangement illuminates the inner surface of the bore in the workpiece to be tested from different illumination directions and generates shadow images of a topography of the inner surface of the bore in the workpiece;
d) the downstream evaluation apparatus determines the topography of the inner surface of the bore in the workpiece based on the shadow images of the topography of the inner surface of the bore in the workpiece recorded by the image recorder; and
e) an advancing apparatus is provided, the advancing apparatus advances the measuring head in the axial direction in a stepwise and in a continuous manner.

18. The testing device according to claim 17, wherein:
a) the illumination apparatus has a first light source arrangement for illuminating the inner surface from a first illumination direction, and a second light source arrangement for illuminating the inner surface from a second illumination direction.

19. The testing device according to claim 17, wherein:
a) the first light source arrangement is configured for radially illuminating the inner surface, and the second light source arrangement is configured for tangentially illuminating the inner surface in the peripheral direction.

* * * * *